United States Patent [19]

Evans

[11] Patent Number: 5,032,583

[45] Date of Patent: Jul. 16, 1991

[54] 2,N-6-DISUBSTITUTED ADENOSINES AND THEIR ANTIHYPERTENSIVE METHODS OF USE

[75] Inventor: Brian Evans, Buntingford, England

[73] Assignee: Glaxo Group Limited, England

[21] Appl. No.: 431,089

[22] Filed: Nov. 3, 1989

Related U.S. Application Data

[63] Continuation of Ser. No. 288,240, Dec. 22, 1988, abandoned.

[30] Foreign Application Priority Data

Dec. 23, 1987 [GB] United Kingdom ............... 8729994

[51] Int. Cl.$^5$ .................. A61K 31/70; C07H 19/167
[52] U.S. Cl. ...................................... 514/46; 536/26;
536/24; 514/45
[58] Field of Search .................... 536/24, 26; 514/46

[56] References Cited

U.S. PATENT DOCUMENTS

| | | | |
|---|---|---|---|
| 3,838,147 | 9/1974 | Pohlke et al. | 536/26 |
| 3,901,876 | 8/1975 | Vorbruggen | 536/26 |
| 3,929,763 | 12/1975 | Fauland et al. | 536/26 |
| 3,929,764 | 12/1975 | Fauland et al. | 536/26 |
| 3,988,317 | 10/1976 | Kampe et al. | 536/26 |

FOREIGN PATENT DOCUMENTS

| | | |
|---|---|---|
| 0179667 | 4/1986 | European Pat. Off. |
| 2052596 | 5/1972 | Fed. Rep. of Germany |
| 2148838 | 4/1973 | Fed. Rep. of Germany |
| 2426682 | 12/1975 | Fed. Rep. of Germany |
| 1552957 | 1/1969 | France |
| 1325970 | 8/1973 | United Kingdom |
| 1385830 | 3/1975 | United Kingdom |
| 1416422 | 12/1975 | United Kingdom |

Primary Examiner—Johnnie R. Brown
Assistant Examiner—L. Eric Crane
Attorney, Agent, or Firm—Bacon & Thomas

[57] ABSTRACT

Compounds of formula (I)

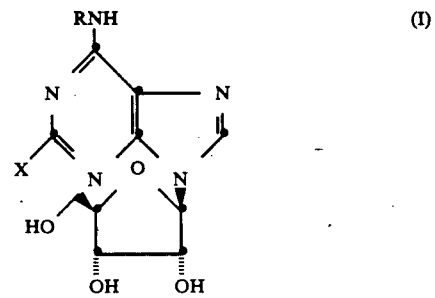

wherein X represents a hydrogen or chlorine atom, or a methyl group; and R represents a cycloalkyl or cycloalkenyl ring containing 5 to 8 carbon atoms, which ring is substituted by a hydroxy group, and is optionally substituted by a $C_{1-6}$alkyl group and salts and solvates thereof.

The new compounds have been found to exhibit activities such as an anti-lipolytic action.

Processes for preparing the compounds of formula (I) and compositions containing them are also described.

18 Claims, No Drawings

2,N-6-DISUBSTITUTED ADENOSINES AND THEIR ANTIHYPERTENSIVE METHODS OF USE

This application is a continuation of application Ser. No. 07/288,240, filed Dec. 22, 1988, now abandoned.

This invention relates to novel adenosine derivatives, to processes for their preparation, to pharmaceutical compositions containing them and to their use in medicine. In particular, the invention relates to compounds which act as inhibitors of lipolysis.

GB-A-1143150 discloses compounds of formula

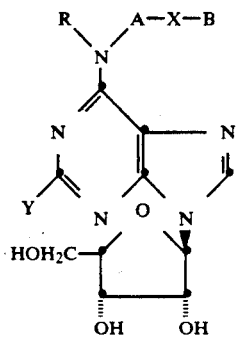

wherein Y is a halogen atom or a hydroxyl group, R is a hydrogen atom or an alkyl group, A is a saturated or unsaturated straight- or branched-chain or cyclic aliphatic hydrocarbon group which may be substituted by one or more hydroxyl and/or acyloxy groups, X is a valency bond or an oxygen or sulphur atom or an optionally alkylated or acylated imino group and B is a hydrogen atom or an optionally substituted phenyl or naphthyl group.

These compounds are said to exhibit cardiac and circulatory actions.

No compound is exemplified in which —A—X—B represents a cycloalkyl or cycloalkenyl ring substituted by a hydroxy group and there is no suggestion in GB-A-1143150 that any of the compounds disclosed possess anti-lipolytic activity. We have now found a novel group of N(6)-monosubstituted adenosine derivatives which differ structurally from those previously described, and which act as inhibitors of lipolysis.

Thus the invention provides compounds of formula (I):

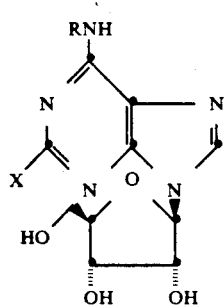

wherein X represents a hydrogen or chlorine atom, or a methyl group; and R represents a cycloalkyl or cycloalkenyl ring containing 5 to 8 carbon atoms, which ring is substituted by a hydroxy group, and is optionally substituted by a $C_{1-6}$alkyl group; and salts and solvates thereof, in particular physiologically acceptable salts and solvates thereof.

It will be appreciated that when the group R contains one or more asymmetric carbon atoms, then the invention includes all resulting diastereoisomers and mixtures thereof.

As used herein, the term cycloalkenyl refers to a 5 to 8 membered ring containing a single double bond.

Particular examples of the group R include:

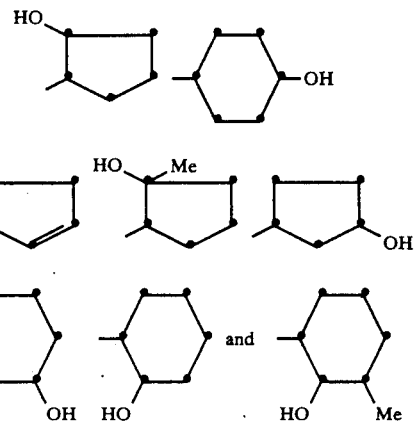

Suitable physiologically acceptable salts of the compounds of general formula (I) include acid addition salts derived from inorganic or organic acids, such as sulphates, phosphates, benzoates, camphorsulphonates, p-toluenesulphonates, methanesulphonates, sulphamates, ascorbates, tartrates, citrates, maleates, salicylates, fumarates, succinates, lactates, glutarates, glutaconates, acetates or tricarballylates. The solvates may be, for example, hydrates.

A preferred class of compounds of formula (I) is that in which X represents a hydrogen atom or a methyl group, more preferably a hydrogen atom.

A further preferred class of compounds of formula (I) is that in which the group R represents a cycloalkyl or cycloalkenyl ring containing 5 or 6 carbon atoms, substituted by a hydroxy group at any available position. The ring may be optionally substituted by a $C_{1-3}$alkyl (e.g. methyl or ethyl) group. More preferably, R represents a cycloalkyl ring containing 5 or 6 carbon atoms substituted by a hydroxy group at any available position, and optionally substituted by a $C_{1-3}$alkyl (e.g. methyl) group on the same carbon atom as the hydroxy group.

A particularly preferred class of compounds of formula (I) is that in which R represents a 2-hydroxycyclopentyl, 4-hydroxycyclohexyl, 3-hydroxycyclohexyl or 2-hydroxy-2-methylcyclopentyl group.

Preferred compounds according to the invention are:
N-[(1S, trans)-2-hydroxycyclopentyl]adenosine;
N-[(1R, trans)-2-hydroxycyclopentyl]adenosine; and mixtures thereof;
N-(trans-4-hydroxycyclohexyl)-2-methyladenosine;
N-(cis-4-hydroxycyclohexyl)adenosine;
N-(cis-2-hydroxycyclopentyl)adenosine;
N-(trans-3-hydroxycyclohexyl)adenosine;
N-(trans-hydroxy-2-methylcyclopentyl)adenosine;
N-(cis-2-hydroxycyclohexyl)adenosine;
and physiologically acceptable salts and solvates thereof.

Particularly preferred compounds according to the invention are:

N-[(1S, trans)-2-hydroxycyclopentyl]adenosine and
N-[(1R, trans)-2-hydroxycyclopentyl]adenosine and mixtures
thereof, more especially N-[1S,trans)-2-hydroxycyclopentyl]adenosine and physiologically acceptable salts and solvates thereof.

Tests in animals have shown that the compounds according to the invention are inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose and ketone body levels and therefore may be of value in the therapy of diabetes. Since anti-lipolytic agents have hypolipidaemic and hypofibrinogenaemic activity, the compounds may also show anti-atherosclerotic activity.

The anti-lipolytic activity of compounds according to the invention has been demonstrated by their ability to lower the concentration of non-esterified fatty acids (NEFA) in starved rats dosed orally.

An especially important group of compounds on account of their marked anti-lipolytic effect, is that group of compounds of formula (I) in which X represents a hydrogen atom, and R represents a cyclopentyl ring substituted by a hydroxy group and optionally also substituted by a $C_{1-6}$alkyl (e.g. methyl) group.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina. The compounds may also inhibit renin release and thus be of use in the therapy of hypertension and heart failure. The compounds may also be useful as CNS agents (e.g. as hypnotics, sedatives, analgetics and/or anti-convulsants).

Accordingly, the invention provides a compound of formula (I) or a physiologically acceptable salt or solvate thereof for use in the treatment of human or animal subjects suffering from a condition in which there is an advantage in decreasing plasma free fatty acid concentration and/or reducing heart rate and conduction.

In a further aspect, the invention provides a method of treatment of a human or animal subject suffering from a condition in which there is an advantage in decreasing plasma free fatty acid concentration and/or reducing heart rate and conduction which comprises administering to the subject an effective amount of a compound of formula (I) or a physiologically acceptable salt or solvate thereof.

It will be appreciated that reference to treatment includes prophylaxis as well as the alleviation of established symptoms.

In yet a further aspect, the invention provides a pharmaceutical composition comprising, as active ingredient, at least one compound of formula (I) or a physiologically acceptable salt or solvate thereof in association with a pharmaceutical carrier and/or excipient for use in human or veterinary medicine.

Compositions according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 2 mg to 2 g, preferably 10 mg to 1 g, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a physiologically acceptable salt or solvate thereof for the manufacture of a medicament for the treatment of human or animal subjects suffering from a condition in which there is an advantage in decreasing plasma free fatty acid concentration and/or reducing heart rate and conduction.

The compounds of formula (I) and physiologically acceptable salts or solvates thereof may be prepared by the processes described hereinafter, said processes constituting a further aspect of the invention. In the following description, the groups X and R are as defined for compounds of formula (I) unless otherwise stated.

According to a first general process (A), a compound of formula (I) may be prepared by reacting a compound of formula (II):

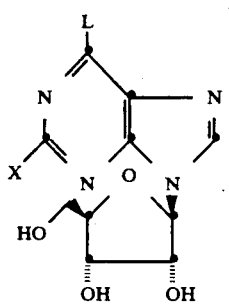

(II)

wherein L represents a leaving group such as a halogen atom (e.g. a chlorine atom) or a trimethylsilyloxy group, or a protected derivative thereof, with a compound of formula RNH₂ or a salt or protected derivative thereof, under basic conditions, followed where necessary by removal of any protecting groups as described, for example, in process (D). The compounds of formulae (II) and RHN₂ may be protected, for example as described hereinafter. Thus a compound of formula (II) may be protected for example, as the isopropylidene, tribenzoyl or triacetyl derivative, and a compound of formula RNH₂ may be protected, for example as an N-benzyl derivative.

The reaction may conveniently be effected either in the absence or presence of a solvent such as an alcohol (e.g. a lower alkanol such as propan-2-ol or t-butanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine, or alkylene oxides such as ethylene oxide or propylene oxide.

Compounds of formulae (II) and RNH₂, and protected derivatives thereof, are either known compounds or may be prepared by conventional methods, for example as described hereinafter.

According to another general process (B), a compound of formula (I) wherein X represents a hydrogen atom or a methyl group, may be prepared by rearranging a compound of formula (III):

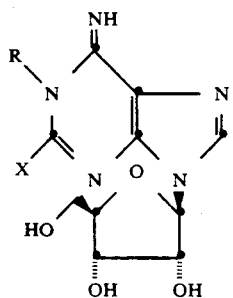

(III)

wherein X represents a hydrogen atom or a methyl group, or a protected derivative thereof, by heating in the presence of a base such as an alkali metal hydroxide (e.g. sodium hydroxide) or an alkali metal carbonate (e.g. sodium carbonate) and conveniently in a solvent such as an aqueous alcohol (e.g. ethanol), followed where necessary by removal of any protecting groups.

The reaction may conveniently be effected at a temperature in the range 50° to 100° C.

Compounds of formula (III) and protected derivatives thereof may be prepared by reacting a compound of formula (IV):

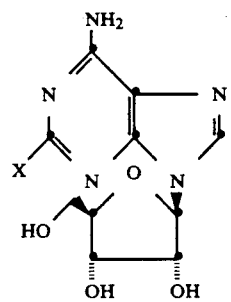

(IV)

wherein X represents a hydrogen atom or a methyl group, or a protected derivative thereof, with a strong base such as a Grignard reagent (e.g. isopropylmagnesium chloride), followed by reaction with an alkylating agent capable of introducing the desired group R, such as an appropriate halohydrin or epoxide. Thus, for example, when R is a 2-hydroxycyclopentyl group, this compound may be cyclopenteneoxide.

Compounds of formula (IV) and protected derivatives thereof are either known compounds or may be prepared by conventional procedures.

According to another general process (C), a compound of formula (I) may be prepared from another compound of formula (I) using conventional procedures.

Thus, for example, hydrogenation may be used to prepare a compound of formula (I) in which R represents a substituted cycloalkyl group from the corresponding compound of formula (I) in which R represents a substituted cycloalkenyl group. Hydrogenation may also be used to prepare a compound of formula (I) in which X represents a hydrogen atom from the corresponding compound of formula (I) in which X represents a chlorine atom. In this latter case, the hydrogenation is effected in the presence of an acid scavenger such as sodium acetate.

Hydrogenation according to general process (C) may be effected using conventional procedures, for example using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium choride may be used. The hydrogenation will generally be effected in a solvent such as an alcohol (e.g. methanol or ethanol), an ether (e.g. tetrahydrofuran or dioxan), an ester (e.g. ethyl acetate) or water, or in a mixture of solvents (e.g. a mixture of two or more of those just described), at a temperature in the range −20° to +100° C., and at a pressure of from 1 to 10 atmospheres.

It should be appreciated that in the above transformations it may be necessary or desirable to protect any sensitive groups in the compound in question to avoid undesirable side reactions. For example, it may be necessary to protect the hydroxyl groups in a compound of formula (II), (III) or (IV), or the nitrogen atom in a compound of formula RNH₂.

Examples of suitable hydroxyl protecting groups include acyl (e.g. hydrocarbylcarbonyl groups such as acetyl, benzoyl, pivaloyl and octanoyl); alkyl (e.g. methyl, t-butyl and methoxymethyl); aralkyl (e.g. benzyl, diphenylmethyl, triphenylmethyl and p-methoxyphenyldiphenylmethyl); and silyl (e.g. trialkylsilyl such as t-butyldimethylsilyl) groups. In addition, two adjacent hydroxyl groups may be protected with an alkylidene (e.g. isopropylidene) group or with a disiloxanyl (e.g. 1,1,3,3-tetraisopropyldisilox-1,3-diyl) group. Particularly convenient protected derivatives of the compounds of formulae (II), (III) and (IV) are the isopropylidene, triacetyl, tribenzoyl and tri-t-butyldimethylsilyl derivatives.

Examples of suitable N-protecting groups for a compound of formula $RNH_2$ include arylmethyl (e.g. benzyl); acyl (e.g. acetyl); and silyl (e.g. trimethylsilyl) groups.

Thus according to another general process (D), a compound of formula (I) may be prepared by the removal of any protecting groups from a protected derivative of the compound of formula (I). Deprotection may be effected using conventional techniques such as those described in "Protective Groups in Organic Synthesis" by T. W. Greene (John Wiley and Sons, 1981).

Thus, for example, acyl OH-protecting groups may be removed by using methanol in the presence of a base such as potassium carbonate, t-butylamine or ammonia. An isopropylidene group may be removed by acid-catalysed hydrolysis (e.g. using trifluoroacetic or sulphuric acid). t-Butyldimethylsilyl groups may be removed by alkaline hydrolysis (e.g. using sodium hydroxide in ethanol).

An N-benzyl group may be cleaved by hydrogenolysis in the presence of a catalyst (e.g. palladium on charcoal), for example, as described in process (C). An N-acyl group (e.g. an acetyl group) or a trimethylsilyl group may be removed under acidic or basic conditions (e.g. using dilute hydrochloric acid or sodium hydroxide). Specific diastereoisomers of a compound of formula (I) may be obtained by conventional methods for example, by synthesis from an appropriate asymmetric starting material using any of the processes described herein, or where appropriate by separation of a mixture of isomers of a compound of formula (I) by conventional means e.g. by fractional crystallisation or chromatography.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of formula (I) may be prepared by reacting a compound of formula (I) with an appropriate acid or base in the presence of a suitable solvent such as acetonitrile, acetone, chloroform, ethyl acetate or an alcohol (e.g. methanol, ethanol or isopropanol).

Physiologically acceptable salts may also be prepared from other salts, including other physiologically acceptable salts of the compounds of formula (I), using conventional methods.

The invention is further illustrated by the following Intermediates and Examples. Temperatures are in °C. Organic extracts were dried, where indicated, over anhydrous sodium sulphate. Thin layer chromatography (t.l.c.) was carried out on silica. Column chromatography was carried out on silica (Merck 7734) unless otherwise stated and the silica onto which reaction mixtures were adsorbed was also Merck 7734 unless otherwise stated. Flash column chromatography (FCC) was carried out on silica (Merck 9385). Florisil was 60–100 mesh (obtained from BDH). The following abbreviations are used: System A-dichloromethane:ethanol:0.88 ammonia solution; System B-ethyl acetate:methanol; DEA-N,N-diisopropylethylamine; THF-tetrahydrofuran $^1$H-N.m.r. spectra were obtained at 250 MHz for dilute solutions in dimethyl sulphoxide.

INTERMEDIATE 1

3-Aza-2-oxabicyclo[2.2.1]heptane-3-carboxylic acid, (phenylmethyl) ester

Azodicarbonamide (5.0 g) was stirred with a solution of potassium hydroxide (7.0 g) in water (12 ml) at 4°. After stirring in the ice bath for 1 h the mixture was diluted with ice/water (30 ml) and the solution was filtered. The filtrate was diluted with cool (2°) ethanol (100 ml) and the resultant solid was filtered off, washed with ethanol, methanol and ether to give potassium azodicarboxylate (6.9 g). This was then mixed with 3-aza-2-oxabicyclo[2.2.1]hept-5-ene-3-carboxylic acid, (phenylmethyl) ester (0.82 g) in dry pyridine (60 ml), and acetic acid (2.02 g) was added with stirring at room temperature. After one hour a further portion of glacial acetic acid (2.02 g) was added and the reaction mixture was stirred for 15.5 h. The mixture was evaporated to dryness under reduced pressure. Further acetic acid was then added to quench the remaining yellow colour of the diimide precursor. The residue was partitioned between 0.5M citric acid (75 ml) and ethyl acetate (75 ml) and the organic phase was separated, dried, and concentrated in vacuo. The residue was purified by FCC eluting with ethyl acetate:cyclohexane (1:2) to give the title compound (0.69 g) as an oil.
T.l.c. (cyclohexane:ethyl acetate, 2:1) Rf 0.25.

INTERMEDIATE 2

N-(cis-3-Hydroxycyclopentyl)carbamic acid, (phenylmethyl) ester

A solution 3-aza-2-oxabicyclo[2.2.1]heptane-3-carboxylic acid, (phenylmethyl) ester (0.5 g) in glacial acetic acid (0.5 ml) was added to a stirred suspension of powdered zinc (0.35 g) in a mixture of acetic acid and water (1:1; 4 ml), and the mixture was stirred at 60° for 7.5 h. Additional zinc powder (0.14 g) and acetic acid (1 ml) were added and stirring was continued for a further 16.5 h. After cooling to room temperature, the mixture was filtered and the excess of zinc washed with 2M hydrochloric acid (20 ml). The combined filtrate and washings were neutralised with 8% sodium carbonate and extracted into ethyl acetate (3×30 ml). The combined organic extracts were washed with brine (30 ml), dried and concentrated in vacuo. Purification by FCC eluting with ethyl acetate: cyclohexane (1:1) gave an oil (120 mg) which solidified upon standing and was recrystallised from cyclohexane to give the title compound (70 mg), m.p. 62°–63°.

INTERMEDIATE 3 trans-N-[3-(Formyloxy)cyclopentyl]carbamic acid, (phenylmethyl) ester

Diethyl azodicarboxylate (1.78 g) was added dropwise to a stirred solution of N-(cis-3-hydroxycyclopentyl)carbamic acid, (phenylmethyl) ester (1.19 g), triphenylphosphine (2.68 g) and formic acid (0.47 g) in THF (65 ml) under nitrogen at room temperature. The resulting solution was stirred for 2 h, and concentrated to give a residue which was stirred in ether (20 ml) at ca −10° under nitrogen for 1 h. The mixture was diluted with cyclohexane (20 ml), and the solid was filtered off and washed with ether:cyclohexane (1:1; 3×ca. 20 ml). The combined filtrate and washings were concentrated, and the resultant residue was purified by FCC eluting with ethyl acetate:cyclohexane (2:3) to give the title compound (1.18 g), m.p. 45°–48°.

INTERMEDIATE 4 trans-3-Aminocyclopentanol hydrochloride

A solution of trans N-[3-(formyloxy)cyclopentyl]carbamic acid, (phenylmethyl) ester (1.1 g) in ethanol (40 ml) was stirred with potassium carbonate (0.25 g) at room temperature for 1 h. The mixture was then filtered and concentrated in vacuo. The resulting semi-solid was dissolved in ethyl acetate (50 ml), filtered, and the filtrate was concentrated in vacuo to leave a solid which was hydrogenated in ethanol (50 ml) with 5% palladium on carbon (200 mg) as catalyst at one atmosphere pressure for 20 h. The catalyst was then changed for fresh 5% palladium on carbon (200 mg) and the hydrogenation was continued for a further 20 h. The reaction mixture was filtered and the filtrate was concentrated in vacuo. The residue was purified by FCC eluting with System A (40:10:1) to give an oil (0.26 g) which was diluted with ethanol (40 ml), acidified with 3M ethanolic hydrogen chloride and concentrated in vacuo to give the title compound (0.34 g).

T.l.c. (System A, 40:10:1) Rf 0.1.

INTERMEDIATE 5

[1α,2α,6β]-2-Methyl-6-[(phenylmethyl)amino]cyclohexanol

A mixture of 2-methyl-7-oxabicyclo[4.1.0]heptane (5.0 g), benzylamine (5.15 g) and water (0.8 ml) was heated under reflux for 7.5 h under nitrogen. Purification by FCC eluting with System B (40:1) gave the title compound (3.9 g) as a solid.

T.l.c. (System B, 20:1) Rf 0.33.

INTERMEDIATE 6

[1α,2α,6β]-6-Amino-2-methylcyclohexanol hydrochloride

A solution of [1α,2α,6β]-2-methyl-6-[(phenylmethyl)amino]cyclohexanol (3.5 g) in absolute ethanol (75 ml) was hydrogenated over 10% palladium on charcoal (50% aqueous paste; 1.3 g) in absolute ethanol (25 ml). The mixture was filtered and evaporated to ca. 100 ml. The solution was acidified with ca. 1M ethanolic hydrogen chloride and the solvent was evaporated in vacuo to give a solid which was recrystallised twice from isopropanol-ethyl acetate to give the title compound, m.p. 194°–195°.

INTERMEDIATE 7

1,6-Dihydro-1-(trans-2-hydroxycyclopentyl)-6-imino-9-[[2,3,5-tris-0-(1,1-dimethylethyl)dimethylsilyl]-β-D-ribofuranosyl]-9H-purine Isopropylmagnesium chloride (2.0M solution in THF; 1.23 ml) was added to a cooled solution of 2′,3′,5′-tris-0-[(1,1-dimethylethyl)dimethylsilyl]adenosine in dry THF (20 ml). After stirring for 15 min, a solution of cyclopenteneoxide (0.206 g) in dry THF (5 ml) was added, and the solution was heated under reflux for 3 days. Ethyl acetate (50 ml) and water (50 ml) were added and the phases were separated. The organic phase was washed with water (50 ml), dried and evaporated under reduced pressure. Purification of the residue by column chromatography eluting with System A (800:40:1) gave the title compound as a foam (0.56 g).

T.l.c. (System A, 800:40:1) Rf 0.54.

INTERMEDIATE 8

N-[(1S,trans)-2-Hydroxycyclopentyl]-2′,3′-O-[1-methylethylidene]adenosine

A mixture of 6-chloro-9-[2′,3′-O-(1-methylethylidene)-β-D-ribofuranosyl]purine (25.0 g), (1S, trans)-2-aminocyclopentanol hydrochloride (12.64 g), DEA (29.67 g) and chloroform (250 ml) was stirred and heated at reflux under nitrogen for 20 h. The resultant solution was cooled to ca. 20° and washed with 1M aqueous citric acid (2×150 ml). The combined aqueous layers were back extracted with chloroform (2×100 ml). The combined organic layers were concentrated under reduced pressure to give a foam. Isopropyl acetate (750 ml) was added to the foam and the resultant solution was concentrated to 500 ml under reduced pressure to give a slurry which was cooled to 5°. The solid was isolated by filtration, washed with isopropyl acetate (2×50 ml) and dried in vacuo at 40° to give the title compound (24.8 g), m.p. 177°–178°.

INTERMEDIATE 9

2′,3′,5′-Tri-0-acetyl-N-[(1S,trans)-2-hydroxycyclopentyl]adenosine

A mixture of 2′,3′,5′-tri-0-acetyl-6-chloropurine-β-D-riboside (1.06 g), (1S,trans)-2-aminocyclopentanol hydrochloride (0.41 g) and sodium bicarbonate (0.50 g) in isopropanol (12 ml) was heated under reflux for 4 h. The mixture was evaporated and the residue was purified by column chromatography eluting with System B (50:1) to give the title compound (0.71 g) as a glass.

T.l.c. (System B, 50:1) Rf 0.21.

INTERMEDIATE 10

N-[(1S,trans)-2-Hydroxycyclopentyl]-N-(phenylmethyl)adenosine

A mixture of 6-chloropurine-β-D-riboside (688 mg), (1S,trans)-2[(phenylmethyl)amino]cyclopentanol (516 mg) and DEA (0.67 g) in isopropanol (20 ml) was stirred and heated under reflux under nitrogen for 7 days. The mixture was then adsorbed onto silica and purified by column chromatography eluting with System A (75:8:1) to give a foam (0.86 g) which was repurified by column chromatography eluting with ethyl acetate: ethanol (4:1) to give an oil (700 mg). This was dissolved in ethyl acetate (10 ml) and the resulting solution was poured into cyclohexane (30 ml) to give the title compound (597 mg) as a solid.

T.l.c. (System A, 75:8:1) Rf 0.21.

EXAMPLE 1

N-[(1S,trans)-2-Hydroxycyclopentyl]adenosine

A mixture of 6-chloropurine-β-D-riboside (2.87 g) and (1S,trans)-2-aminocyclopentanol hydrochloride (1.38 g) was heated under reflux in isopropanol (100 ml) containing DEA (3.87 g) for 18 h. Silica gel (20 g) was added to the cooled solution and the suspension was evaporated under reduced pressure. The dried support was added to a column of silica gel (250 g) and was eluted with System B (9:1). Appropriate eluates were collected and evaporated under reduced pressure yielding a white powder. Crystallisation from ethyl acetate and methanol gave the title compound as a white powder (2.3 g), m.p. 163°–164°.

T.l.c. (System B, 9:1) Rf 0.23.

EXAMPLE 2

N-[(1R,trans)-2-Hydroxycyclopentyl]adenosine

A mixture of 6-chloropurine-$\beta$-D-riboside (2.87 g) and (1R,trans)-2-aminocyclopentanol hydrochloride (1.38 g) was heated under reflux in isopropanol (100 ml) containing DEA (3.87 g) for 18 h. On cooling, a powder was deposited which was filtered off, washed with propan-2-ol (50 ml) and dried in vacuo to give the title compound (2.35 g), m.p. 235°–236°.

T.l.c. (System B, 9:1) Rf 0.23.

EXAMPLE 3

N-(trans-5-Hydroxycyclopent-2-enyl)adenosine

A mixture of 6-chloropurine-$\beta$-D-riboside (0.86 g), trans-3-aminocyclopent-1-en-4-ol, 4-methylbenzenesulphonate (0.69 g), and DEA (0.52 g) in isopropanol (35 ml) was heated at reflux with stirring overnight under nitrogen. The cooled mixture was concentrated in vacuo to give an oil (2.56 g) which was purified by column chromatography on silica (Merck 9385, deactivated with 1% triethylamine), eluting with System B (10:1) to give a solid (0.522 g). This was recrystallised from ethyl acetate (15 ml) to give the title compound (185 mg).

T.l.c. on silica deactivated with 1% triethylamine (System B, 10:1) Rf 0.25.

$^1$H-N.m.r. $\delta$2.12–2.28(1H,m), 2.65–2.80(1H,m), 3.5–3.78(2H,m), 4.0(1H,ddd), 4.18(1H,m), 4.35(1H,m), 4.63(1H,q), 5.05(1H,brm), 5.2–5.3 and 5.4–5.55(4H,2xm), 5.7 and 5.86(2H,2xm), 5.92(1H,d), 7.92(1H,brd), 8.25(1H,brs), 8.4(1H,s).

EXAMPLE 4

N-(cis-2-Hydroxycyclopent-4-enyl)adenosine, (Diastereoisomers 1 and 2)

A mixture of 6-chloropurine-$\beta$-D-riboside (2.01 g), cis-2-hydroxycyclopent-4-enylamine hydrochloride (1.42 g), DEA (2.71 g) and isopropanol (100 ml) was heated under reflux for 20 h. The resulting solution was adsorbed onto silica and purified by column chromatography eluting with System A (30:8:1) to give a foam which was triturated with System B (10:1; 20 ml) to give crystals$^1$ (1.05 g).

The mother liquors were evaporated to dryness and the resulting solid was recrystallised from methanol (5 ml) to give Diastereoisomer 1 of the title compound (0.31 g).

Optical rotation C=0.5465% (w/v) in DMSO $[\alpha]_D^{20°} = -1.5°$.

Analysis found: C,50.5; H,5.5; N,19.5; $C_{15}H_{19}N_5O_5 \cdot 0.4CH_4O \cdot 0.1H_2O$ requires C,50.8; H, 5.8; N,19.2%.

The crystals$^1$ (1.05 g) were recrystallised from methanol (20 ml) to give Diastereoisomer 2 of the title compound (0.46 g), m.p. 212.5°–214°.

Optical rotation C=0.52957% (w/v) in DMSO $[\alpha]_D^{20°} = -131.8°$.

Analysis found: C,50.9; H,5.5; N,19.9; $C_{15}H_{19}N_5O_5 \cdot 0.2H_2O$ requires C,51.05; H,5.5; N,19.8%.

EXAMPLE 5

N-(cis-2-Hydroxycyclopent-4-enyl)adenosine

A mixture of 6-chloropurine-$\beta$-D-riboside (2.01 g), cis-2-hydroxycyclopent-4-enylamine hydrochloride (1.42 g), DEA (3.19 g) and isopropanol (100 ml) was heated under reflux for 22 h. The resulting solution was adsorbed onto silica and purified by column chromatography eluting with System B (5:1) to give the title compound (1.7 g) as a foam.

T.l.c. (System A, 50:8:1) Rf 0.11.

Analysis found: C,49.5; H,5.6; N,18.9; $C_{15}H_{19}N_5O_5 \cdot 0.9H_2O$ requires C,49.3; H,5.7; N,19.2%.

EXAMPLE 6

N-(trans-2-Hydroxycyclopentyl)-2-methyladenosine

A mixture of 6-chloro-2-methyl-9-($\beta$-D-ribofuranosyl)-9H-purine (902 mg), trans-2-aminocyclopentanol (404 mg), DEA (517 mg) and isopropanol (35 ml) was heated under reflux with stirring for 22 h under nitrogen. Additional trans-2-aminocyclopentanol (202 mg) and DEA (259 mg) were added and heating under reflux was maintained for a further 5 h. The cooled mixture was concentrated in vacuo and the residual foam (1.9 g) was purified by column chromatography on silica (Merck 9385, deactivated with triethylamine) eluting with System B (10:1) to give a solid (1.01 g). This was repurified by column chromatography on silica (Merck 9385) eluting with System B (10:1) to give the title compound (0.57 g), m.p. 188°–192°.

Analysis found: C,52.6; H,6.5; N,19.0; $C_{16}H_{23}N_5O_5$ requires C,52.6; H,6.3; N,19.2%.

EXAMPLE 7

N-(trans-Hydroxy-2-methylcyclopentyl)adenosine

A mixture of 6-chloropurine-$\beta$-D-riboside (1.0 g) and trans-2-amino-1-methylcyclopentanol hydrochloride (0.55 g) in isopropanol (50 ml) containing DEA (1.35 g) was heated under reflux for 24 h. The suspension was adsorbed onto silica and purified by column chromatography eluting with System B (9:1) to give a powder. Crystallisation from isopropyl acetate and methanol gave the title compound (0.75 g).

T.l.c. (System B, 9:1) Rf 0.35.

Analysis found: C,50.9; H,6.6; N,18.0; $C_{16}H_{23}N_5O_5 \cdot 0.1C_5H_{10}O_2 \cdot 0.75$ $H_2O$ requires C,51.1; H,6.5; N,18.05%.

EXAMPLE 8

N-(cis-3-Hydroxycyclopentyl)adenosine

6-Chloropurine-$\beta$-D-riboside (1.0 g), cis-3-aminocyclopentanol (0.48 g) and DEA (0.96 g) were stirred under reflux in isopropanol (50 ml) for 30 h. The solution was allowed to cool to room temperature and concentrated in vacuo. Purification by FCC eluting with System A (50:10:1) afforded the title compound (0.9 g) as a foam.

T.l.c. (System A, 50:10:1) Rf 0.4.

Analysis found: C,50.3; H,6.3; N,18.9; $C_{15}H_{21}N_5O_5 \cdot 0.5H_2O \cdot 0.2C_4H_8O_2$ requires C,50.1; H,6.2; N,19.0%.

EXAMPLE 9

N-(trans-4-Hydroxycyclohexyl)adenosine

A mixture of 6-chloropurine-$\beta$-D-riboside (1.15 g), trans-4-aminocyclohexanol hydrochloride (0.61 g), triethylamine (1.12 ml) and isopropanol (50 ml) was heated under reflux for 18 h. More trans-4-aminocyclohexanol hydrochloride (0.30 g) and triethylamine (0.56 ml) were added and heating was continued for 7 h. Further trans-4-aminocyclohexanol hydrochloride (0.30 g) and triethylamine (0.56 ml) were added and heating was continued for a further 18 h. The resulting mixture was adsorbed onto silica and purified by column chromatography eluting with System A (30:8:1) to give a foam. This was washed in hot ether which was then evaporated to leave the title compound (0.82 g) as a solid.

T.l.c. (System A, 30:8:1) Rf 0.41.

Analysis found: C,52.2; H,6.5; N,18.7; $C_{16}H_{23}N_5O_4$ requires: C,52.6; H,6.3; N,19.0%.

EXAMPLE 10

N-(trans-2-Hydroxycyclohexyl)adenosine

A mixture of 6-chloropurine-$\beta$-D-riboside (1.15 g), trans-2-hydroxycyclohexylamine hydrochloride (0.67 g), DEA (1.14 g) and isopropanol (50 ml) was heated under reflux for 22 h. The resulting solution was adsorbed onto silica and purified by column chromatography eluting with System A (30:8:1) to give a foam which was dissolved in ethanol (50 ml) and again adsorbed onto silica. Further purification by column chromatography eluting with System B (5:1) gave a solid which was dissolved in ethyl acetate (20 ml) and precipitated with cyclohexane (80 ml) to give the title compound (0.48 g).

T.l.c. (System B, 10:1) Rf 0.10.

Analysis found: C,53.1; H,6.7; N,17.9; $C_{16}H_{23}N_5O_5.0.2C_6H_{12}.0.2H_2O$ requires C,53.5; H,6.7; N,18.15%.

EXAMPLE 11

N-(cis-2-Hydroxycyclohexyl)adenosine

A mixture of 6-chloropurine-$\beta$-D-riboside (1.15 g), cis-2-hydroxycyclohexylamine hydrochloride (0.67 g), DEA (1.14 g) and isopropanol (50 ml) was heated under reflux for 30 h. The resulting solution was adsorbed onto silica and purified by column chromatography eluting with System B (2:1) to give a solid which was dissolved in ethanol (100 ml) and again adsorbed onto silica. Further purification by column chromatography eluting with System B (5:1) gave a solid which was recrystallised from methanol (20 ml) to give the title compound (0.32 g), m.p. 210°–211°.

T.l.c. (System B, 5:1) Rf 0.27.

EXAMPLE 12

N-(trans-3-Hydroxycyclohexyl)adenosine

A mixture of 6-chloropurine-$\beta$-D-riboside (1.0 g) and trans-3-aminocyclohexanol hydrochloride (0.53 g) in isopropanol (50 ml) containing DEA (1.35 g) was heated under reflux for 3 days. The resulting suspension was adsorbed onto silica and purified by column chromatography eluting with System A (30:8:1) to give a foam. Crystallisation from a mixture of isopropanol and isopropyl acetate gave the title compound (0.7 g).

T.l.c. (System A, 50:8:1) Rf 0.27.

Analysis found: C,51.8; H,6.6; N,18.2; $C_{16}H_{23}N_5O_5.0.1\ C_5H_{10}O_2.0.5H_2O$ requires C,51.5; H,6.55; N,18.2%.

EXAMPLE 13

N-(cis-3-Hydroxycyclohexyl)adenosine

6-Chloropurine-$\beta$-D-riboside (1.0 g) and cis-3-aminocyclohexanol hydrochloride (0.53 g) were treated according to the method of Example 12 (except that the mixture was heated under reflux for 2 days) to give the title compound (0.58 g).

T.l.c. (System A, 30:8:1) Rf 0.27.

Analysis found: C,52.1; H,6.9; N,17.2; $C_{16}H_{23}N_5O_5.0.3C_5H_{10}O_2.0.5H_2O$ requires C,51.9; H,6.7; N,17.3%.

EXAMPLE 14

N-(trans-4-Hydroxycyclohexyl)-2-methyladenosine

A mixture of 6-chloro-2-methyl-9-($\beta$-D-ribofuranosyl)-9H-purine (902 mg), trans-4-aminocyclohexanol hydrochloride (1.14 g) and DEA (1.94 g) in isopropanol (50 ml) was heated at reflux with stirring under nitrogen for 17 h. The resulting cooled reaction mixture was adsorbed onto silica (Merck 9385) and purified by column chromatography on silica (Merck 9385) eluting with System B (10:1 then 8:1) to give the title compound (0.9 g) as a solid.

T.l.c. (System B, 5:1) Rf 0.2.

Analysis found: C,52.3; H,6.7; N,16.7; $C_{17}H_{25}N_5O_5.0.33C_4H_8O_2.0.67$ requires C,52.3; H,6.95; N,16.6%.

EXAMPLE 15

N-(cis-2-Hydroxycyclopentyl)adenosine

A mixture of N-(cis-2-hydroxycyclopent-4-enyl)adenosine (1.6 g), 5% platinum on charcoal (0.3 g) and ethanol (80 ml) was stirred in the presence of hydrogen for 20 h. The resulting mixture was filtered and the filtrate was evaporated. The residue was dissolved in methanol (50 ml) and the solution was evaporated to yield the title compound (1.2 g) as a foam.

T.l.c. (System A, 30:8:1) Rf 0.30.

Analysis found C,49.6; H,6.15; N,19.1; $C_{15}H_{21}N_5O_5.0.3CH_4O.0.5H_2O$ requires C,49.6; H,6.3; N,18.9%.

EXAMPLE 16

N-(trans-2-Hydroxycyclopentyl)adenosine

A mixture of 6-chloropurine-$\beta$-D-riboside (1.15 g), trans-2-aminocyclopentanol (0.41 g), triethylamine (0.41 g) and isopropanol (50 ml) was heated under reflux for 20 h. Further quantities of trans-2-aminocyclopentanol (0.08 g) and triethylamine (0.08 g) were added and heating was continued for 4 h. The resulting mixture was adsorbed onto silica and purified by column chromatography eluting with System A (30:8:1) to give a solid (0.48 g). This was repurified by column chromatography eluting with System B (12:1) to give a foam which was triturated with ether to give the title compound (0.31 g) as a 2:1 mixture of diastereoisomers.

T.l.c. (System B, 12:1) Rf 0.35.

Analysis found C,50.8; H,6.25; N,18.8; $C_{15}H_{21}N_5O_5.0.17(C_2H_5)_2O.\ 0.5H_2O$ requires C,50.5; H,6.4; N,18.8%.

EXAMPLE 17

N-(trans-3-Hydroxycyclopentyl)adenosine

6-Chloropurine-$\beta$-D-riboside (0.63 g), trans-3-aminocyclopentanol hydrochloride (0.3 g) and DEA (0.63 g) were stirred under reflux in isopropanol (30 ml) for 3.5 days. The reaction mixture was allowed to cool to room temperature, whereupon a precipitate formed which was dissolved by the addition of methanol. The solution was adsorbed onto silica (Merck 9385) and purified by FCC eluting with System B (3:1) to give a powder. Final purification by column chromatography on silica (Merck 7734) eluting with System B (3:1) gave the title compound (44 mg), m.p. 208°–210°, as a 52:48 mixture of diastereoisomers.

$^1$H-N.m.r. $\delta$1.4–2.2(6H,m) 3.5–3.78(2H,m), 3.99(1H,m), 4.1–4.2(1H,m), 4.2–4.3(1H,m), 4.55(1H,d), 4.62(1H,m), 4.8(1H,brm), 5.22(1H,d), 5.42–5.52(2H,m), 5.9(1H,d), 7.82(1H,brd), 8.2(1H,brs), 8.83(1H,s).

EXAMPLE 18

N-(cis-4-Hydroxycyclohexyl)adenosine

6-Chloropurine-$\beta$-D-riboside (1.0 g), cis-4-aminocyclohexanol hydrochloride (0.53 g) and DEA (0.96 g) were stirred under reflux in isopropanol (50 ml) for 20 h. After cooling to room temperature, the solution was adsorbed onto Florisil and purified by column chromatography eluting with System A (50:8:1) to give a foam. Further purification by column chromatography as before gave the title compound (0.55 g) as a foam.

T.l.c. (System A, 50:8:1) Rf 0.07.

Analysis found: C,51.9; H,7.0; N,17.5; $C_{16}H_{23}N_5O_5.0.55EtOH.0.3H_2O$ requires C,51.85; H,6.8; N,17.7%.

EXAMPLE 19

[1$\alpha$,2$\beta$,3$\beta$]-N-[2-Hydroxy-3-methylcyclohexyl]adenosine

A mixture of 6-chloropurine-$\beta$-D-riboside (1.0 g), [1$\alpha$,2$\alpha$,6$\beta$]-6-amino-2-methylcyclohexanol hydrochloride (0.58 g) and DEA (0.9 g) in isopropanol (35 ml) was heated under reflux for 26 h. The resulting solution was adsorbed onto Florisil and purified by column chromatography eluting with System B (20:1 then 10:1) to give the title compound (0.884 g), m.p. 128°–133°, as a 47:53 mixture of diastereoisomers.

T.l.c. (System B, 5:1) Rf 0.65.

Analysis found C,53.0; H,6.8; N,16.8; $C_{17}H_{24}N_5O_5.0.3C_4H_8O_2.0.5H_2O$ requires C,52.8; H,6.7; N,16.9%.

EXAMPLE 20

2-Chloro-N-[(1S,trans)-2-hydroxycyclopentyl]adenosine

A mixture of 2,6-dichloro-9-(2',3',5'-tri-0-benzoyl-$\beta$-D-ribofuranosyl)-9H-purine (1.68 g), (1S,trans)-2-aminocyclopentanol hydrochloride (380 mg) and DEA (1.4 ml) in isopropanol (25 ml) was stirred and heated under reflux for 5.5 h under nitrogen. The mixture was concentrated in vacuo and a solution of the residue in methanol (25 ml) was treated with aqueous ammonia (2 ml). The resulting mixture was stirred for 16 h and was then concentrated in vacuo. The residue was purified by column chromatography eluting with System A (75:8:1) to give a foam (570 mg). This was dissolved in ethyl acetate (10 ml) and the resulting solution was poured into cyclohexane (80 ml) to give a solid. The solid and crystallisation liquor were combined, concentrated in vacuo and the residue was dissolved in methanolic ammonia (10 ml). The solution was allowed to stand for 4 days and was then concentrated in vacuo to give an oil (570 mg) which was purified by column chromatography eluting with System A (50:8:1) to give the title compound (212 mg).

T.l.c. (System A, 50:8:1) Rf 0.16.

Analysis found: C,45.9; H,5.55; N,16.7; $C_{15}H_{20}ClN_3O_5.0.5C_2H_6O.0.6H_2O$ requires C,45.85; H,5.7; N,16.7%.

EXAMPLE 21

2-Chloro-N-[(1R,trans)-2-hydroxycyclopentyl]adenosine

A mixture of 2,6-dichloro-9-(2',3',5'-tri-0-benzoyl-$\beta$-D-ribofuranosyl)-9H-purine (1.68 g), (1R-trans)-2-aminocyclopentanol hydrochloride (380 mg) and DEA (1.4 ml) in isopropanol (25 ml) was stirred and heated under reflux for 5 h under nitrogen. The reaction mixture was concentrated in vacuo and a solution of the residue in methanol (10 ml) was treated with saturated methanolic ammonia (20 ml), and kept at room temperature for 8 days. The mixture was concentrated in vacuo and the residue was purified by column chromatography eluting with System A (50:8:1) to give a glass (770 mg). This was dissolved in hot ethyl acetate (40 ml) and the resulting solution was poured into cyclohexane (160 ml) to give a solid (447 mg). This was combined with the residue from the evaporation of the crystallisation liquor and the resulting solid (1.2 g) was adsorbed onto silica and purified by column chromatography eluting with System A (75:8:1 then 50:8:1) to give a glass (830 mg). This was dissolved in hot ethyl acetate (20 ml), and the resulting solution was poured into cyclohexane (160 ml) to give the title compound (598 mg) as a solid.

T.l.c. (System A, 50:8:1) Rf 0.20.

Analysis found: C,47.6;H,5.5; N,17.35; $C_{15}H_{20}ClN_5O_5.0.1C_6H_{12}$ requires C,47.55; H,5.4;N,17.75%.

EXAMPLE 22 trans-2-Chloro-N-(4-hydroxycyclohexyl)adenosine

A mixture of 2,6-dichloro-9-(2',3',5'-tri-0-benzoyl-$\beta$-D-ribofuranosyl)-9H-purine (1.68 g), trans-4-aminocyclohexanol hydrochloride (424 mg) and DEA (1.4 ml) in isopropanol (25 ml) was stirred and heated under reflux under nitrogen for 4.5 h. The reaction was allowed to cool for 30 min and was concentrated in vacuo to give a foam which was dissolved in methanol (10 ml), and saturated methanolic ammonia (20 ml) was added. The resulting solution was kept at room temperature for 6 days, and was then adsorbed onto silica and purified by column chromatography eluting with System A (75:8:1 then 30:8:1) to give an oil which crystallised on standing to give a solid (1.02 g). This was dissolved in ethanol, filtered and the filtrate was concentrated in vacuo and triturated with ethyl acetate to give a solid. The solid was repurified by column chromatography eluting with System B (5:1) to give the title compound (405 mg), m.p. 203°–204°.

Analysis found: C,47.9; H,5.6; N,15.75; $C_{16}H_{22}ClN_5O_5.0.35C_4H_8O_2.0.4H_2O$ requires C,47.75; H,5.9; N,16.0%.

EXAMPLE 23

N-[(1S,trans)-2-Hydroxycyclopentyl]adenosine fumaric acid salt (1:1)

Fumaric acid (1.2 g) was added to a refluxing solution of N-[(1S,trans)-2-hydroxycyclopentyl]adenosine (7.03 g) in isopropanol (105 ml). The resulting hot solution was filtered, and the filtrate was cooled and allowed to crystallise. After 2 h at 20° the crystalline product was isolated by filtration, washed with isopropanol (10 ml) and dried in vacuo at 50° for 20 h to give the title compound (6.5 g), m.p. 179°–180°. The chromatographic behaviour of this salt resembled that of an authentic sample of the free base.

EXAMPLE 24

N-[1S,trans)-2-Hydroxycyclopentyl]adenosine (1S)-(+)-10-camphorsulphonic acid salt A mixture of N-[(1S,trans)-2-hydroxycyclopentyl]adenosine (3.51 g) and (1S)-(+)-10-camphorsulphonic acid (2.44 g) in isopropanol (35 ml) was heated at reflux under nitrogen until a clear solution was obtained. The solution was diluted with isopropyl acetate (50 ml) and the mixture was cooled to ca. 25° with stirring. The resultant crystalline solid was isolated by filtration, washed with isopropanol: isopropyl acetate (1:2; 2×15 ml) and dried in vacuo at 40° to give the title compound (5.31 g), m.p. 150°–152°.

Analysis found: C,51.25;H,6.7;N,11.9;S,5.3; $C_{25}H_{37}N_5O_9S$ requires C,51.4;H,6.4;N,12.0;S,5.5%.

EXAMPLE 25

N-[(1S,trans)-2-Hydroxycyclopentyl]adenosine

A mixture of 6-chloro-9-[2',3'-0-(1-methylethylidene)-$\beta$-D-ribofuranosyl]purine (8.0 g), (1S,trans)-2-aminocyclopentanol hydrochloride (4.0 g), DEA (12.7 ml), chloroform (70 ml) and isopropanol (10 ml) was stirred and heated at reflux, under nitrogen, for 18 h. The solution was then cooled to 25° and washed with 1M citric acid (2×80 ml); the aqueous layers were back extracted sequentially with chloroform (2×40 ml). The combined chloroform solutions were extracted with 1M sulphuric acid (50 ml+25 ml), and the acid extracts were washed sequentially with chloroform (40 ml). The combined sulphuric acid solution was stored at 20° for 2 h. Potassium carbonate (50 g) was added to the acid solution and the mixture was extracted with isopropanol (2×50 ml). The isopropanol extracts were combined and concentrated under reduced pressure to give an oil which was diluted with methanol (50 ml) and reconcentrated. The residue was dissolved in methanol (20 ml) at reflux and ethyl acetate (80 ml) was added. The solution was filtered and stirred to induce crystallisation. After 4 h the crystalline solid was isolated by filtration, washed with ethyl acetate (20 ml) and dried in vacuo at 40° to afford the title compound (4.81 g), m.p. 162°–163°. Its chromatographic behaviour resembled that of authentic material.

EXAMPLE 26

N-[(1S,trans)-2-Hydroxycyclopentyl]adenosine

A suspension of 6-chlorpurine-$\beta$-D-riboside (30.0 g), (1S,trans)-2-aminocyclopentanol hydrochloride (15.0 g) and anhydrous sodium carbonate (30.0 g) in t-butanol (300 ml) was stirred at reflux under nitrogen for 21 h. The suspension was allowed to cool to 72°, filtered, and the collected solid was washed with hot (75°) t-butanol (2×60 ml). The combined filtrate and washings were concentrated in vacuo to give a foam. This was dissolved in methanol (55 ml) at reflux and then ethyl acetate (550 ml) was added dropwise over 0.5 h whilst maintaining reflux (ca.65°). The resultant suspension was stirred under nitrogen for 1.5 h and cooled to 25°; it was then aged at 20°–25° for 1.5 h. The solid was filtered off, washed with System B (10:1; 2×60 ml) and dried in vacuo at 50° to give the title compound (31.50 g). Its chromatographic behaviour resembled that of authentic material.

Analysis found: C,51.2;H,6.0;N,19.8; $C_{15}H_{21}N_5O_5$ requires C,51.3;H,6.0;N,19.9%.

EXAMPLE 27

N-(Trans-2-hydroxycyclopentyl)adenosine

A solution of 1,6-dihydro-1-(trans-2-hydroxycyclopentyl)-6-imino-9-[[2,3,5-tris-O-[1,1-dimethylethyl)-dimethylsilyl]-$\beta$-D-ribofuranosyl]-9H-purine (0.3 g) in ethanol (20 ml) containing 2N sodium hydroxide (5 ml) was heated under reflux for 5 h. The resulting suspension was adsorbed onto silica and purified by column chromatography eluting with System B (9:1) to give a powder. This was crystallised from ethyl acetate-methanol to give the title compound (0.11 g) as a 65:35 mixture of 1R:1S diastereoisomers.

T.l.c. (System B, 9:1) Rf 0.26.

Analysis found: C,49.5; H,6.1; N,19.6; $C_{15}H_{21}N_5O_5.0.6H_2O$ requires C,49.7; H,6.2; N,19.3%.

Hplc:

Column: Spherisorb −C8 5 $\mu$m (25 cm×4.6 mm)

Mobile phase: 10% acetonitrile in triethylammonium phosphate buffer (pH 3.5)

Flow rate: 1 ml/min

Retention times: (1R, trans) 10.2 min (65%); (1S, trans) 8.4 min (35%).

EXAMPLE 28

(1S,trans)-N-(2-Hydroxycyclopentyl)adenosine

A solution of (1S, trans)-2-chloro-N-(2-hydroxycyclopentyl)adenosine (102 mg) and sodium acetate (108 mg) in water (3.2 ml) and ethanol (8.2 ml) was hydrogenated over 10% palladium on carbon (50% aqueous 100 mg) for 21 h. The mixture was filtered and the filtrate was concentrated to give a solid which was dissolved in hot methanol (4 ml). The resulting solution was filtered, and ethyl acetate (2 ml) was added to the hot solution to precipitate the title compound (64 mg).

T.l.c. (System B, 9:1) Rf 0.24.

Hplc:

Column: Spherisorb −C8 5 $\mu$m (25 cm×4.6 mm)

Mobile phase: 25% acetonitrile in triethylammonium phosphate buffer (pH 3.5)

Flow rate: 1 ml/min

Retention time: 9.6 min (which was the same as that of authentic material).

EXAMPLE 29

N-[(1S,trans)-2-Hydroxycyclopentyl]adenosine

N-[(1S,trans)-2-Hydroxycyclopentyl]-2',3'-O-[1-methylethylidene]adenosine (24.0 g) was dissolved in a mixture of trifluoroacetic acid (14.2 ml) and water (120 ml) at ca. 20° and the mixture was stirred under nitrogen for 3.5 h. Anhydrous potassium carbonate (28.0 g) was added and the solution was extracted with dichloromethane (48 ml). Further potassium carbonate (68 g)

was added and the aqueous layer was extracted with isopropanol (2×48 ml). The combined isopropanol extracts were washed with saturated aqueous potassium carbonate (24 ml) and the two aqueous phases were extracted sequentially with more isopropanol (48 ml). The combined isopropanol extracts were concentrated under reduced pressure to an oil. Methanol (120 ml) was added to the oil and the solvent was removed under reduced pressure and then at high vacuum to yield a semi-solid. This was dissolved in hot ethyl acetate (120 ml) and the hot solution was clarified by filtration. The filtrate was seeded and stirred at ca. 20° for 5 h. The solid product was isolated by filtration, washed with System B (8:1; 50 ml) and dried in vacuo to give the title compound (17.3 g), m.p. 159°–162°. Its chromatographic behaviour resembled that of authentic material.

EXAMPLE 30

N-[(1S,trans)-2-Hydroxycyclopentyl]adenosine

A solution of 2′,3′,5′-tri-O-acetyl-N-[(1S,trans)-2-hydroxycyclopentyl]adenosine (0.34 g) in methanol (7 ml) containing t-butylamine (3 ml) was allowed to stand at 23° for 16 h. The solution was evaporated to dryness and residual t-butylamine was removed azeotropically with methanol to leave a glass. Crystallisation of a sample of this glass (0.19 g) from a mixture of methanol and ethyl acetate (1:20) gave the title compound (0.15 g), m.p. 160°–163°. Its chromatographic behaviour resembled that of authentic material.

EXAMPLE 31

N-[(1S,trans)-2-Hydroxycyclopentyl]adenosine

A solution of N-[(1S,trans-2-hydroxycyclopentyl]-N-(phenylmethyl)adenosine (0.2 g) in ethanol (50 ml) was hydrogenated at atmospheric pressure and 45° using 10% palladium on charcoal (0.1 g) as catalyst. After 18 h the mixture was filtered and the filtrate was evaporated. The residue was crystallised from a mixture of ethyl acetate and methanol to give the title compound (0.075 g), m.p. 162°–163°. Its chromatographic behaviour resembled that of authentic material.

EXAMPLE 32

N-(trans-2-Hydroxycyclooctyl)adenosine

A mixture of trans-2-aminocyclooctanol (0.34 g), 6-chloropurine-$\beta$-D-riboside (0.70 g) and DEA (0.60 g) was heated under reflux in isopropanol (25 ml) for 24 h. The resulting solution was adsorbed onto Florisil and purified by column chromatography eluting with System B (9:1) to give the title compound (0.43 g).

T.l.c. (System B, 9:1) Rf 0.38

Analysis found: C, 53.05; H, 7.0; N, 16.9; $C_{18}H_{27}N_5O_5.075H_2O$ requires C,53.1; H,7.1;N,17.2%.

The following examples illustrate pharmaceutical formulations according to the invention, containing N-[(1S,trans)-2-hydroxycyclopentyl]adenosine as the active ingredient. Physiologically acceptable salts and/or solvates of this compound, and other compounds of formula (I) and their physiologically acceptable salts and/or solvates may be formulated in a similar manner.

1. Oral Capsule

| | Per capsule |
|---|---|
| Active ingredient | 50 mg |
| Magnesium stearate | 0.5 mg |
| Starch 1500* | 49.5 mg |

*a form of directly compressible starch.

Blend the sieved drug with the excipients. Fill the blend into appropriate size hard gelatin capsule filling machine.

2. Oral Syrup

| | per 5 ml dose |
|---|---|
| Active ingredient | 25 mg |
| Hydroxypropylmethylcellulose USP (viscosity type 4000) | 25 mg |
| Buffer | |
| Flavour | |
| Colour | As required |
| Preservative | |
| Sweetener | |
| Purified water | to 5 ml |

Disperse the hydroxypropylmethylcellulose in hot water, cool and then mix with an aqueous slution containing the active ingredient and the other components of the formulation. Adjust the resultant solution to volume and mix. Clarify the syrup by filtration and pack into glass bottles with suitable child resistant closures.

3. Oral Tablet

| | Per tablet |
|---|---|
| Active ingredient | 100 mg |
| Croscarmellose sodium | 30 mg |
| Magnesium stearate | 3 mg |
| Microcrystalline cellulose to tablet core weight of | 300 mg |

Sieve all the ingredients and blend together in a suitable blender until homogenous. Compress with appropriate punches on an automatic tablet machine. The tablets may be covered in a thin polymer coat applied by the usual film coating techniques. A pigment may be included in the filmcoat.

4. Sub-lingual Tablet

| | Per tablet |
|---|---|
| Active ingredient | 2 mg |
| Hydroxypropylmethylcellulose | 5 mg |
| Magnesium stearate | 1 mg |
| Mannitol to tablet core weight of | 65 mg |

Sieve the active ingredient and blend with the mannitol and hydroxypropylmethylcellulose. Add suitable volumes of purified water to granulate. After drying, screen the granules, blend with the magnesium stearate and compress with appropriate punches on an automatic tablet machine.

5. Solution for Inhalation

| | Per 2 ml dose |
|---|---|
| Active ingredient | 22 mg |
| Sodium chloride | qs |
| Sodium hydroxide solution | to pH 7.2 |
| pH 7.2 phosphate buffer | 0.2 ml |
| Water suitable for injection | to 2 ml |

I claim:

1. A compound selected from compounds of formula (I)

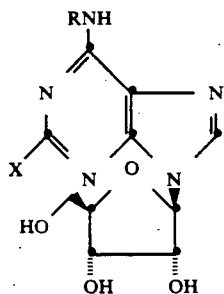

wherein X is selected from the group consisting of hydrogen, chlorine and methyl; and R is selected from the group consisting of cycloalkyl and cycloalkenyl rings each containing 5 to 8 carbon atoms, which rings are substituted by a hydroxy group, and optionally substituted by a $C_{1-6}$alkyl group; and salts and solvates thereof.

2. A compound of claim 1 wherein X is selected from the group consisting of hydrogen and methyl; and physiologically acceptable salts and solvates thereof.

3. A compound of claim 2 wherein X is hydrogen; and physiologically acceptable salts and solvates thereof.

4. A compound of claim 1 wherein said cycloalkyl or cycloalkenyl ring contains 5 or 6 carbon atoms; and physiologically acceptable salts and solvates thereof.

5. A compound of claim 4 wherein R is a cycloalkyl ring containing 5 or 6 carbon atoms substituted by a hydroxy group and optionally substituted by a $C_{1-3}$ alkyl group on the same carbon atom as the hydroxy group; and physiologically acceptable salts and solvates thereof.

6. A compound of claim 5 wherein R is selected from the group consisting of 2-hydroxycyclopentyl, 4-hydroxy-cyclohexyl, 3-hydroxycyclohexyl and 2-hydroxy-2-methylcyclopentyl; and physiologically acceptable salts and solvates thereof.

7. A compound of claim 3 wherein R is a cyclopentyl ring substituted by a hydroxy group and optionally substituted by a $C_{1-6}$ alkyl group; and physiologically acceptable salts and solvates thereof.

8. The compound of claim 1 which is N-[(1S, trans)-2-hydroxycyclopentyl]adenosine and physiologically acceptable salts and solvates thereof.

9. A compound of claim 1 selected from
N-[(1S, trans)-2-hydroxycyclopentyl]adenosine;
N-[(1R, trans)-2-hydroxycyclopentyl]adenosine;
and mixtures thereof; and physiologically acceptable salts and solvates of any of these.

10. A compound of claim 1 selected from the group consisting of
N-(trans-4-hydroxycyclohexyl)-2-methyladenosine;
N-(cis-4-hydroxycyclohexyl)adenosine;
N-(cis-2-hydroxycyclopentyl)adenosine;
N-(trans-3-hydroxycyclohexyl)adenosine;
N-(trans-hydroxy-2-methylcyclopentyl)adenosine;
N-(cis-2-hydroxycyclohexyl)adenosine;
and physiologically acceptable salts and solvates of any of these.

11. A pharmaceutical composition comprising, as active ingredient, an effective amount of a compound of formula (I) as claimed in claim 1 in association with pharmaceutical carrier or excipient.

12. A composition as claimed in claim 11 wherein the compounds of formula I are selected from the group consisting of:
N-[(1S, trans)-2-hydroxycyclopentyl]adenosine;
N-[(1R, trans)-2-hydroxycyclopentyl]adenosine;
N-(trans-4-hydroxycyclohexyl)-2-methyladenosine;
N-(cis-4-hydroxycyclohexyl)adenosine;
N-(cis-2-hydroxycyclopentyl)adenosine;
N-(trans-3-hydroxycyclohexyl)adenosine;
N-(trans-2-hydroxy-2-methylcyclopentyl)adenosine;
N-(cis-2-hydroxycyclohexyl)adenosine;
and physiologically acceptable salts and solvates thereof.

13. A composition according to claim 12 wherein the active ingredient is administered to a human subject at a unit dose of 2 mg to 2 g per 70 kg body weight, from 1 to 4 times per day.

14. A composition according to claim 13 wherein the unit dose is 10 mg to 1 g per 70 kg body weight, from 1 to 4 times per day.

15. A composition as claimed in claim 12 wherein the composition is formulated for oral administration.

16. A method of treatment of a human or a animal subject suffering from hyperlipidemias or cardiovascular disorders including cardiac arrythmias, angina, hypertension and heart failure, wherein an effective amount of a compound of claim 1 or a physiologically acceptable salt or solvate thereof is administered to the human or animal subject.

17. The method of claim 16 wherein the compound of claim 8 is employed.

18. The method of claim 16 wherein a compound of claim 9 or 10 is employed.

* * * * *